(12) United States Patent
Wendel et al.

(10) Patent No.: US 9,784,753 B2
(45) Date of Patent: Oct. 10, 2017

(54) BIOLOGICAL SYSTEM TO TEST IN VITRO IF A SUBSTANCE IS IMMUNE REACTIVE

(76) Inventors: Albrecht Wendel, Tübingen (DE); Thomas Hartung, Constance (DE)

( * ) Notice: Subject to any disclaimer, the term of this patent is extended or adjusted under 35 U.S.C. 154(b) by 1114 days.

(21) Appl. No.: 10/761,237

(22) Filed: Jan. 22, 2004

(65) Prior Publication Data

US 2005/0090020 A1    Apr. 28, 2005

Related U.S. Application Data

(63) Continuation of application No. 08/996,768, filed on Dec. 23, 1997, now abandoned.

(30) Foreign Application Priority Data

Dec. 23, 1996 (DE) .................... 196 54 266

(51) Int. Cl.
| | |
|---|---|
| A61K 35/14 | (2015.01) |
| A61K 35/50 | (2015.01) |
| C12N 5/0789 | (2010.01) |
| G01N 33/96 | (2006.01) |

(52) U.S. Cl.
CPC ......... G01N 33/96 (2013.01); *G01N 2496/05* (2013.01)

(58) Field of Classification Search
CPC ....... A61K 35/14; A61K 35/50; C12N 5/0789

USPC ...... 435/2, 4, 7.1, 7.21, 7.31, 7.32, 7.92, 30, 435/267, 269, 325, 355, 374; 436/8, 11, 436/174, 176, 501; 523/12
See application file for complete search history.

(56) References Cited

U.S. PATENT DOCUMENTS

| | | | |
|---|---|---|---|
| 4,004,975 A | * | 1/1977 | Lionetti et al. ................. 435/2 |
| 4,219,440 A |   | 8/1980 | Runck et al. |
| 4,701,417 A |   | 10/1987 | Portenhauser et al. |
| 4,731,330 A | * | 3/1988 | Hill et al. ..................... 436/16 |
| 4,774,088 A | * | 9/1988 | Vora ........................... 424/529 |
| 5,030,200 A | * | 7/1991 | Judy et al. ................... 604/5.02 |
| 5,192,553 A | * | 3/1993 | Boyse ................. C12N 5/0647 424/529 |
| 5,364,756 A | * | 11/1994 | Livesey et al. ................. 435/2 |

FOREIGN PATENT DOCUMENTS

| | | |
|---|---|---|
| FR | 2 475 737 | 8/1981 |
| WO | 96 17514 | 6/1996 |

OTHER PUBLICATIONS

Scheuning et al. 1992. Blood. vol. 79(11): 3071-3075.*
Kaye et al. 1991. J. of Virological MEthods. vol. 35:217-226.*
Rubinstein et al. 1995. PNAS. vol. 92, pp. 10119-10122.*
Allen et al., (Cryobiology. 1978. vol. 15:375-381).*

* cited by examiner

*Primary Examiner* — J. A. Hines
(74) *Attorney, Agent, or Firm* — Jacobson Holman PLLC

(57) ABSTRACT

Preparations containing deep-frozen blood are used for test procedures for determining blood response.

3 Claims, 2 Drawing Sheets

Figure 1:
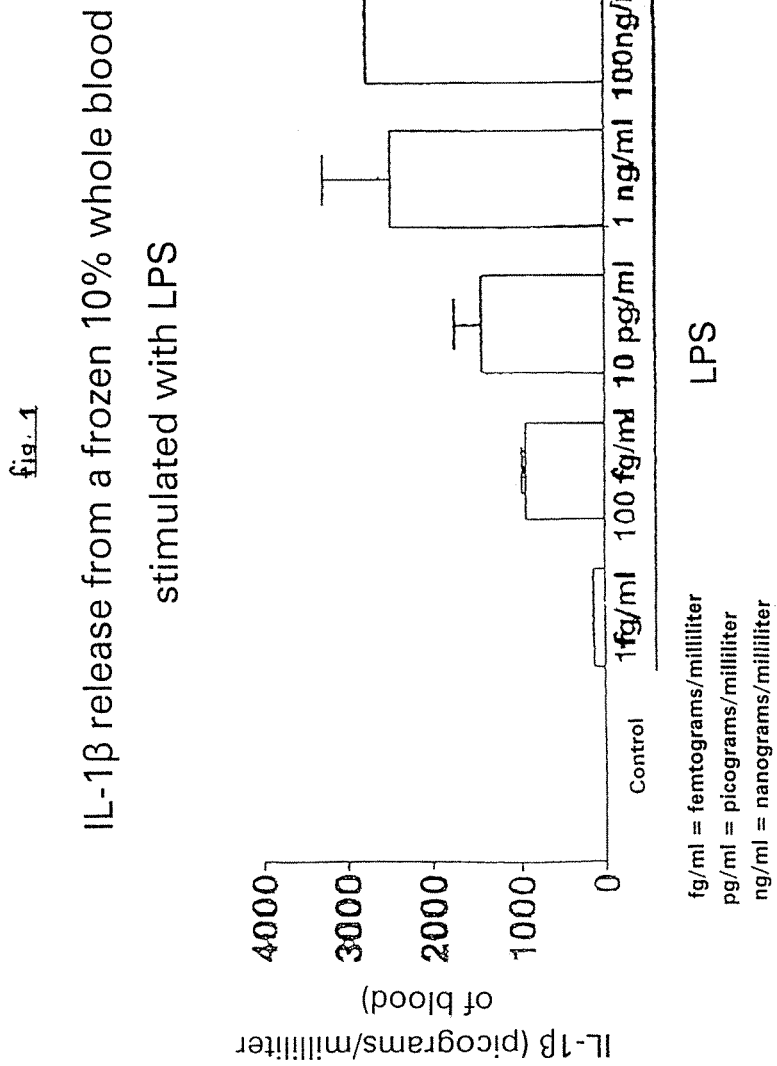

IL-1 release from a frozen 10% human whole blood (huVB) stimulated with LPS
(19 November 1996, 9.1% DMSO, n = 4/1, RMPI 1640)

IL-1 release from a frozen 10% human whole blood stimulated with LPS
(19 November 1996, 9.1% DMSO, n = 4/1, RMPI 1640)

BIOLOGICAL SYSTEM TO TEST IN VITRO IF A SUBSTANCE IS IMMUNE REACTIVE

This is a continuation of Ser. No. 08/996,768, filed, Dec. 23, 1997, abandoned.

The invention is in the field of use of biological systems for tests. Biological systems have long been used to a substantial extent for tests. In these tests the test substances, i. e., the object, material, or device being tested is brought into contact with the biological system. Then the response (which may include non-response) of the system is detected qualitatively and/or quantitatively and evaluated. Such procedures are quite common in dermatology. There, the skin of test subjects, or skin preparations, are used as a biological system to carry out such biological tests, and the response of the skin, or skin preparation in contact with a test material is determined. Incubated chicken eggs are used for tests for mucous membrane irritation. Slaughterhouse products of all types are used as biological systems for a wide range of tests.

This invention concerns the special area of use of blood as a biological test system. For example, it is known that many materials, on contact with human tissues, body fluids and cells, can activate or, in a harmful form, overactivate, the cells of the immune system. Sometimes the response is because the materials themselves stimulate the immune system. At other times, it is because the samples contain immune-stimulating components such as pyrogens, which cause fever. The materials with such a hazard potential include medications in particular, and especially products which can be inhaled, injected, and infused. They include blood replacements and blood substitutes, plastics of various states of aggregation, shapes, and uses, including dispersions and materials such as membranes and prostheses, as well as materials isolated from natural products including plants, animals and humans, or their cell or tissue cultures, isolated products such as vaccines, medications, and genetic therapeutic agents. Materials which cause release of factors such as cytokinins from the leukocytes of the organism when in contact with human tissue, cells, or body fluids are called immunoactivators. More narrowly, they are called pyrogens if the factors released can cause a fever reaction in the organism. Product safety is a pressing requirement in pharmaceuticals, therefore routine individual tests on experimental animals are needed to recognize exceptional contaminated lots. Instead of the pyrogen test on rabbits, as is specified in various pharmacopeias, or the Limulus amebocyte lysate (LAL) test, which, however, detects only one part of the pyrogens and immunoactivators, namely, the endotoxins of Gram-negative bacteria, therefore, the same inventors have previously described a simple, economical, and widely applicable procedure (European Patent 0 741 294 A2, Hartung and Wendel, ALTEX 12, pp. 70-75, 1995) in which blood or blood preparations, as the biological system, are brought into contact with the material to be tested and the release of cytokinins, e. g., leukocyte factors such as interleukin-1 (IL-1β), which produce fever in the organism (endogenous pyrogens) is measured. It is not unusual for the blood response to be needed as soon as possible, and that is quite common in cases where whole blood is required as a biological system for the test. In such cases the test of the test material must be started without delay, and in any case, within a few hours. That leaves no time for thorough checking of the reactivity of the whole blood used, and it is impossible to rule out with the necessary reliability the possibility that the results might be incorrect, with dangerous consequences, or unusable, due to use of blood from a human donor with abnormal reactions such as might be caused by genetic variations, disease, or life style. As in the case of testing of individual lots of pharmaceuticals, mentioned as an example, the danger of improper transportation or storage often requires that the materials be tested before use. But, for the reasons noted above, when blood is used as a biological system, it may not be possible to make a comparison with previous test results with sufficient reliability.

One of the objects of the invention is, accordingly, assuring a smooth and reproducible procedure, ruling out the possibility of error due to abnormal reactions, and pointing out a way that allows test results with the same test material to be compared when blood is used as the biological system for testing. It is intended that repeated tests at various sites be standardized and made possible at various times. Other objectives arise from the advantages pointed out below.

The objective established is attained by use of deep-frozen blood or by a preparation containing deep-frozen blood for biological test procedures for, or with, determination of the blood response on contact with the test material.

Use of deep-frozen blood or a preparation containing such blood makes it possible to have available, at any time, as a biological system, blood which has been previously tested and so is free of abnormal reactions. At the minimum it can be standardized, and then used as a standard reagent. As a large number of completely identical deep-frozen units can be prepared from one lot of blood, the requirement for reproducibility of tests at different times and places can be satisfied. Furthermore, characterization of one such lot with data relevant to the testing opens up a route for comparison with results from use of different lots of blood which have also been adequately characterized.

Whole human or animal blood, from which no components have been separated, has proven to be good as the deep-frozen blood. Freshly drawn blood from human donors is found to be particularly good. The individual components, including the leukocytes, are present in their natural environment, with all the serum components that might influence the action of the test material. Use of deep-frozen whole blood is, therefore, greatly preferred, even though use of leukocytes isolated from the blood is not ruled out. However, most methods of isolation are very expensive for routine testing, so that the use of whole blood is simpler, more reliable for the desired result, and more informative because of the possibility of interactions among the other blood components.

In any case, the deep-frozen product must be thawed to do the biological test procedure. The test material is brought in contact with the blood, or with preparations from it, for a period, and in a manner, that is required to produce an adequate blood response. Contact times of some seconds or minutes can be sufficient, without ruling out multi-hour contact times. Any contact form suitable for attaining the specified purpose can be used. Examples include immersion, flushing, or draining for objects, and mixing with, or adding to the blood or blood preparations and the like for solutions, dispersions, cultures and solids. The usual biological, physical, chemical and/or physicochemical methods for determination and measurement can be used to determine the blood response routinely after even brief incubation of the blood or blood preparation following contact with the test material. These include biological assays and RIA procedures, preferably spectrometric procedures, all procedures which provide qualitative and quantitative measurement of materials released or formed, such as ELISA, or turbidimetric or chemiluminescent procedures, etc.

The preparations with deep-frozen blood, or leukocytes, can contain diluents, components to delay clotting, cryopreservatives, and other materials which are themselves known, as long as they to not affect the test result. Isotonic solutions such as isotonic sodium chloride solution, Ringer's solution and cell culture media such as RMPI 1640 have proved good as diluents. It is advantageous to add the diluent only for performing the test, or after thawing, for instance, at 37° C. The diluents may, for example, make up 5 to 95% by volume of the total preparation. Dilutions of 1 to 10 parts by volume are often used.

The blood or blood preparation can be mixed with cryopreservatives to produce the deep-frozen blood reagent. They may, if necessary, be dispensed in appropriate portions and then deep-frozen. Examples of suitable cryopreservatives include organic solutions, inorganic, even salt-containing solutions, or mixtures of them in variable proportions. For instance, it has proved particularly suitable to use 10% dimethylsulfoxide alone, or glycol or glycerin alone or mixed with dimethylsulfoxide. Controlled slow freezing at, for example, −1° C. per minute is advantageous. A storage temperature of −70° C. has proved good for the frozen blood in a deep-cooling chest, as well as use of condensed or solid gases such as liquid nitrogen or dry ice. The latter is particularly suitable for transport.

The deep-frozen preparation can contain clot-delaying components, or they may be added during or after thawing and during the conduct of the test procedure; for example, during an incubation.

Examples of suitable clotting inhibitors include sodium citrate at, for instance, a final concentration of 0.38% by weight, or heparin, such as sodium heparin, heparin fractions, and the like.

The use according to the invention of preparations containing deep-frozen blood, including deep-frozen blood or deep-frozen leukocytes is used to particular advantage for testing of materials such as the objects, materials, and devices mentioned initially for immunostimulatory or immunomodulatory actions or for qualitative and/or quantitative determination of immune-related effects, through discovering, determining, or evaluation of the blood response on contact of these test materials with the thawed deep-frozen blood or blood preparation.

Other than immunostimulatory effects, such as pyrogenicity, materials can modulate the subsequent activation of the immune system. That may be desirable for immunotherapeutic agents, but is often an undesired toxic effect. Such action should be sought in development of immunopharmacologic agents, but should be ruled out for many other materials.

Immunostimulants are of therapeutic interest, on one hand, for treatment of absolute or relative immune deficiency. On the other hand, immunosuppressive agents and antiinflammatory agents, including antiphlogistics, antirheumatics, and antiallergics, are of interest. Immunotoxic effects of materials, such as substances, have come increasingly to public attention in recent years. There is, as yet, no standardized test system for immunopharmacologic or immunotoxic materials testing. Stimulated whole blood, though, is finding increased scientific use for characterizing the pharmacologic properties of active substances [Hartung et al., Blood 85 (1995) 2482-2489].

Standardization of the blood used is the central problem in use of blood and its factor release for test of immune-related effects such as determination of pyrogens, immunomodulators and immunotoxins.

Here, too, the aforementioned blood preparations can be used, such as whole blood, perhaps diluted with, for example, cell culture media, buffers, or clinical sodium chloride solution. In these cases, the test must particularly often be started within a few hours, so that prior testing of the blood material used for suitability is generally impossible. The objective previously stated is intended to make possible testing of materials for immune-related effects such as pyrogenicity, immunomodulatory or immunotoxic effects, and should make possible the prior testing of the blood, as well as repeated testing of a material at various times and places with the same test blood. That is reliably accomplished by the application according to the invention.

The particular advantage of the invention consists of determination of immune-related effects and data in application of a biological system providing information relevant to human exposure. The measured parameters include cytokinins such as the endogenous pyrogens interleukin-1β, interleukin-6 and tumor necrosis factor; eicosanoids such as the endogenous pyrogen prostaglandin $E_2$, or other substances released from leukocytes, such as degranulation products, soluble receptors, proteins, or low-molecular-weight substances (see also European Patent 0 741 294 A2, which is made a reference here). It is noteworthy that in this procedure not only do the clotting inhibitors citrate and heparin do not have any influence that would falsify the result, but in addition, the deep-freezing preservatives, including the cryopreservatives mentioned, yield a blood which exhibits no disadvantageous effects on the test result after thawing.

The invention has a whole series of other advantages. After thawing of the deep-frozen blood it is again possible to detect inherent physiological reactions of native immune cells under natural conditions and mixing ratios.

Due to deep-frozen preservation it is possible to use the same blood repeatedly at different times and places. Abnormal blood reactions can be recognized in appropriate preliminary tests and the corresponding material can be removed. Standard values for the particular lot of blood can be determined in advance under standardized conditions. It makes it possible to do testing even if it is not immediately possible to draw blood. It is possible to determine not only, for instance, direct immunoactivators but also immunomodulators/immunotoxins through their modulation of the effect of a standard stimulus such as endotoxin (lipopolysaccharides of Gram-negative bacteria). The invention is also suitable for testing pharmacological therapies or exposures ex vivo. In this case, blood is taken from the corresponding patients, subjects, or test animals after administration of the pharmaceutical. It is properly deep-frozen, or cryopreserved, and is only later tested for, as an example, reactivity to a standard stimulus.

Another object of the invention is a preparation containing a collective, containing or comprising deep-frozen blood in the form of standardized unit doses for biological test procedures which involve determination of the blood response on contact with test material.

It is preferable to use fresh whole blood from healthy animals or human donors. It may, if desired, be mixed with cryopreservatives, diluents, and/or clotting inhibitors, as previously described by way of example, measured out, and deep-frozen. The unit dose usually contains from 50 to 500 microliters, preferably 100 microliters, of whole blood, but it is not limited to those quantities. To perform the test procedure, one unit dose of deep-frozen blood is thawed. It is made up, for example, to a desired volume, such as 1 milliliter, with diluents, such as those of the type previously mentioned, and brought into contact with the test material. The blood response is determined in the usual manner and is evaluated. The volume of whole blood that can be drawn at one time from a healthy human donor allows preparation of several thousand unit doses of, for example, 100 microliters. The unit doses can be combined in sets of, for instance, 5, 10, or more unit doses. If desired, data usable for the test procedure can be provided. They can be introduced into commerce while the deep chilling is maintained. The set can, for specific applications, contain not only units with unit doses but also units with a multiple of the unit dose.

The particular unit dose can otherwise contain the same components and have the same composition, and be prepared and used in the same manner, as preparations containing the previously described deep-frozen blood.

EXAMPLE

Citrated blood from healthy donors was mixed with 10% dimethylsulfoxide (Merck, Darmstadt) immediately after it was drawn. Aliquots of 100 microliters were distributed in 2 milliliter reaction vessels (Eppendorf, Hamburg) and transferred to a −70° C. cold box in a commercial freezing system (Mr. Freezy, Nalgene). Thawing was done in a thermoshaker (Eppendorf, Hamburg) at 37° C. Immediately after thawing, 900 microliters of RPMI 1640 (Gibco, Eggenstein), warmed to 37° C., was added. Then the test substances, such as dilutions of a pyrogen, in this case, lipopolysaccharide of *Salmonella abortus equi* (Sigma, Deisenhofen) were added. After a four-hour incubation at 37° C., for example, in an incubator (Heraeus, Fellbach) with 5% carbon dioxide the incubated samples are shaken and centrifuged. Endogenous pyrogens, IL-1β in this case, are determined in the cell-free supernatant, after freezing, if desired. FIG. 1 shows formation of IL-1β in the cryopreserved blood from four healthy donors, depending on the amount of pyrogen added. IL-1β was determined by ELISA (enzyme-linked immunosorbent assay) from antibodies from the company Pharmingen (Hamburg). The test shows release of endogenous pyrogens in the presence of minimal amounts of pyrogens.

Figure 2:
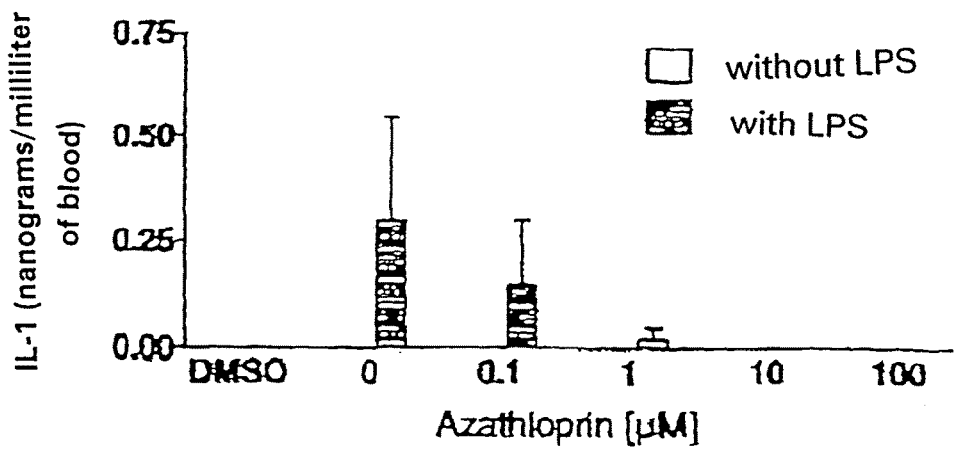
Figure 3:
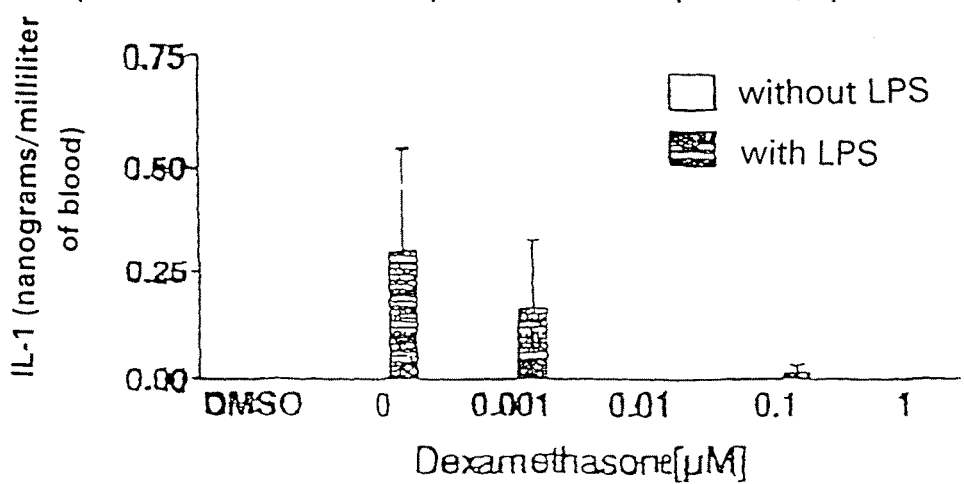

FIGS. 2 and 3 show dependence of release of IL-1 in frozen whole blood stimulated with LPS on the amounts of azathioprin or dexamethasone administered.

What is claimed is:

1. A method of testing whether a substance planned for use in human therapy would cause an immune reaction in humans comprising the steps of:
    selecting a cryopreserved unit dose comprising whole blood including viable leukocytes and a cryopreservative from among a plurality of identical cryopreserved unit doses obtained from a single or pooled sample of blood taken from a human or animal, which single or pooled sample was pre-tested to confirm immune reactivity;
    thawing the cryopreserved unit dose;
    contacting the thawed, cryopreserved unit dose with the substance; and
    determining whether the whole blood in the unit dose has an immune reaction to the substance.

2. The method of claim 1 wherein the whole blood further comprises clotting inhibitors, diluents, or a combination thereof.

3. The method of claim 1, wherein the identical cryopreserved unit doses are standardized.

* * * * *